(12) United States Patent
Cardelius

(10) Patent No.: US 6,820,462 B2
(45) Date of Patent: Nov. 23, 2004

(54) ACOUSTIC GAS MONITOR

(75) Inventor: Erik Cardelius, Stockholm (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 10/384,940

(22) Filed: Mar. 10, 2003

(65) Prior Publication Data

US 2003/0188580 A1 Oct. 9, 2003

(30) Foreign Application Priority Data

Apr. 9, 2002 (SE) .............................................. 0201073

(51) Int. Cl.$^7$ .............................................. G01N 29/02
(52) U.S. Cl. .................................................. 73/24.01
(58) Field of Search ........................... 73/31.07, 24.01, 73/24.04, 24.06, 1.86, 1.83, 629, 645, 625, 579, 597, 598, 24.05, 29.02, 29.01, 29.05, 435.1

(56) References Cited

U.S. PATENT DOCUMENTS 3,367,850 A  2/1968  Johnson
5,285,677 A  2/1994  Oehler
5,581,014 A  12/1996 Douglas
5,689,060 A  11/1997 Matsushima

FOREIGN PATENT DOCUMENTS

EP         0 919 810      6/1999
WO        WO 98/39649    9/1998

Primary Examiner—Helen Kwok
(74) Attorney, Agent, or Firm—Schiff Hardin LLP

(57) ABSTRACT

An acoustic gas monitor has a measurement chamber into which a reference gas of known composition is received and is provided with a wall section for the selective transmission of a gaseous substance to be monitored between the reference gas internal the chamber and a host gas externally of the chamber. An acoustic velocity meter is arranged to supply to an analyzer a signal indicative of an acoustic velocity within the mixture of reference gas and gaseous substance in the chamber. The analyzer being programmed to derive, from the velocity measurement made within the single chamber, information relating to the level of the gaseous substance to be monitored.

7 Claims, 2 Drawing Sheets

ACOUSTIC GAS MONITOR

BACKGROUND OF THE INVENTION

1. Field of the Invention

The present invention relates to an acoustic gas monitor and in particular to a monitor employing the transmission and subsequent detection of acoustic energy through a reference gas of known composition.

2. Description of the Prior Art

It is known, for example from U.S. Pat. No. 5,581,014, to provide a general purpose apparatus for deriving compositional information about a gas mixture that may be used to monitor the presence of a gaseous substance in a host gas, for example the presence of ozone in air or oxygen. This known apparatus has a measurement cell for receiving a gas sample to be measured; a physically separate reference cell for receiving a reference gas of known composition, and means for transmitting and detecting sound waves separately and simultaneously through gas in each of the measurement cell and the reference cell. An analyzer is provided to derive the compositional information about the gas in the measurement cell based on the velocity of sound, as obtained from measured transit times of the sound waves, in each of the measurement and the sample cell.

It is further known, for example from U.S. Pat. No. 5,689,060, to provide a device specifically for monitoring the presence of moisture (the gaseous substance) in air (the host gas). This known device has a reference cell containing datum (reference) air and a measurement cell in to which air having an unknown moisture content is introduced. Acoustic energy is transmitted through air in each of the reference cell and the measurement cell and subsequently detected. An analyzer is provided to derive moisture content information based on the difference in the acoustic velocity between the reference cell and the measurement cell, as obtained from transit time or phase difference measurements. However, changes in the composition of the host gas unrelated to moisture content, for example in the levels of carbon dioxide present in the air, will also cause changes in the measured acoustic velocity and may affect the accuracy of the device.

SUMMARY OF THE INVENTION

The above object is achieved in accordance with the principles of the present invention in an acoustic gas monitor having a measurement chamber for receiving a gaseous substance to be monitored, and an acoustic velocity meter for determining an acoustic velocity within the chamber and for providing an output indicative thereof, wherein the measurement chamber has a wall section for selective transmission of the gaseous substance between a reference gas contained in the interior of the chamber and a host gas disposed at the exterior of the chamber.

By providing for the selective transmission of a gaseous substance to be measured between internal and external a measurement chamber that holds a reference gas, of known composition, then the presence and even the amount of the gaseous substance in a host gas external the chamber can be monitored by monitoring the propagation of acoustic energy in only a single chamber.

Moreover, by providing for the selective transmission into and out of the chamber of only the gaseous substance to be measured. The accuracy of the monitor is made insensitive to unrelated changes in the composition of the host gas.

The selective transmission may be achieved by providing a wall section consisting of a selectively permeable material, chosen to permit the transfer of only the gaseous substance to be monitored between the interior and the exterior of the chamber.

DESCRIPTION OF THE PREFERRED EMBODIMENTS

Figure 1:
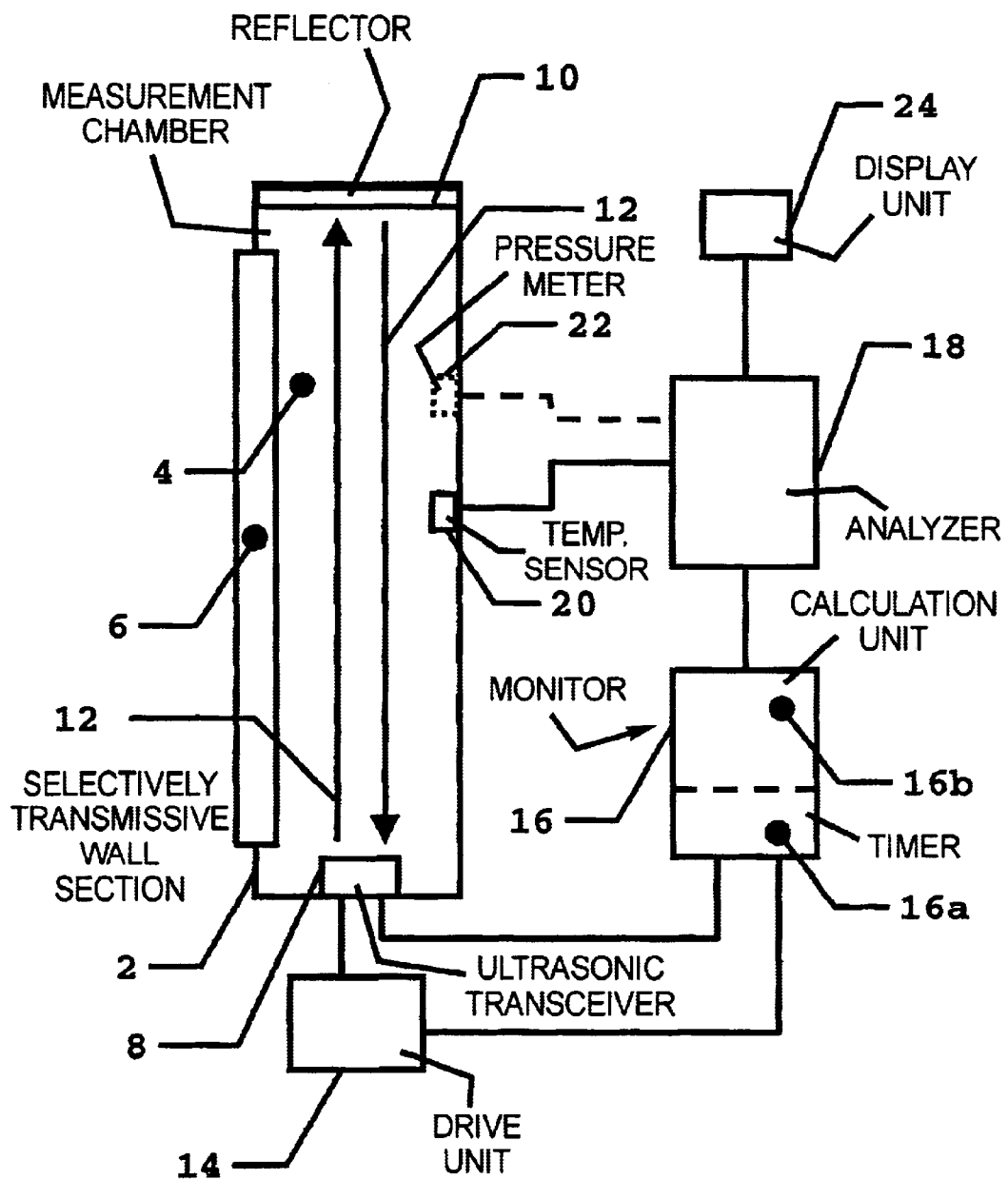
FIG. 1 schematically illustrates of a moisture meter according to the present invention.

As shown FIG. 1, a measurement chamber 2 holding a reference gas 4 is shown as a sealed unit, with respect to the reference gas, and is provided with a wall section 6 that is selectively permeable to the gaseous substance to be measured. In use, the gaseous substance to be measured can be transported through the wall section 6 between the interior and the exterior of the measurement chamber 2 until the concentrations of the gaseous substance internal and external the chamber 2 equalize. In the present example the selectively permeable wall section 6 consists of a material that is selectively permeable to water vapor and can be, for example, NAFION™—an ion exchange polymer commercially available from DuPont of Delaware, USA or GORE-TEX™—a polytetrafluoroethylene based material commercially available from W. L. Gore and Associates of Delaware, USA. It will be appreciated that the selection of the permeable material of the wall section 6 will generally depend on the nature of the reference gas, the host gas, and the gaseous substance to be measured.

An ultrasonic transceiver 8 and reflector 10 are located within the chamber 2 and cooperate to define an acoustic path 12 along which ultrasound waves propagate as the transceiver 8 is operated, in a manner well known in the art of ultrasound metering, alternately as an ultrasound emitter and as an ultrasound receiver under the control of a drive unit 14. In the present example the chamber 2 is formed as an elongate cylinder with the transceiver 8 and reflector 10 located at opposite ends of its long axis, so as to define as long an acoustic path 12 as possible. Other geometries of the chamber 2 and relative locations of the transceiver 8 and reflector 10 are possible in accordance with the invention. Moreover the single transceiver 10 may be substituted with a separate acoustic transmitter and complementary receiver arrangement, such arrangements being well known in the art.

In the present embodiment, the drive unit 14 is connected to a monitor 16 which is also connected to the transceiver 8. In the configuration illustrated in the present embodiment the drive unit 14 is configured to drive the transceiver 8 to generate and transmit an ultrasound pulse and to simultaneously provide a signal to the monitor 16 indicative of this. The monitor 16 is arranged to act as a timer 16a which is started upon the receipt of the signal from the drive unit 14 and which is stopped upon input into the monitor 16 of a signal from the transceiver 8 indicative of its receipt of the transmitted ultrasound pulse after propagation along the acoustic path 12. The thus-determined time t that elapsed between transmission and receipt of the ultrasound pulse is then employed within a calculation unit 16b of the monitor 16 to determine an acoustic velocity V within the chamber 2 according to the equation:

$$V = L/t \qquad (1)$$

where L is the length of the acoustic path 12, the value of which may be preloaded into the calculation unit 16b.

The monitor 16 provides as an output a signal indicative of this determined acoustic velocity V.

It will be appreciated from the above description that the combination of the transceiver 8 and reflector arrangement 10 and the drive unit 14 and the monitor 16 provides an acoustic velocity meter operating in a manner well known in the art. It will be further appreciated that other known acoustic velocity meters may substitute for the one described above in accordance with the invention. A meter in which a means for determining a phase difference between transmitted and received acoustic pulses can be employed in place of the timer 16a, as an example of such a known velocity meter.

An analyzer 18, which may be realized in a suitably programmed microprocessor, is also provided as part of the moisture meter of FIG. 1 and is configured to receive as inputs the output from the monitor 16, indicative of the acoustic velocity, V, and an output from a temperature sensor 20 that is located in thermal communication with interior of the chamber 2 indicative of a sensed temperature, T. The analyzer 18 is programmed to determine a moisture content (volume share), $x_2$, of the reference gas according to the known equation:

$$V = \sqrt{\frac{c_p^* R_M T}{c_v^* M^*}} \text{ where:} \qquad (2)$$

$$M^* = M_1 x_1 + M_2 x_2 \qquad (3)$$

$$c_p^* = \frac{c_{p1} M_1 x_1 + c_{p2} M_2 x_2}{M_1 x_1 + M_2 x_2} \qquad (4)$$

$$c_v^* = \frac{c_{v1} M_1 x_1 + c_{v2} M_2 x_2}{M_1 x_1 + M_2 x_2} \qquad (5)$$

and where, in equations (3)–(5):

the subscripts 1 and 2 refer to the reference gas and the gaseous substance to be measured (here moisture) respectively;

M is the molecular weight;

$C_p$ is the specific heat capacity at constant pressure;

$C_v$ is the specific heat capacity at constant volume; and x is the volume fraction of the total amount of gas, thus $$x_2 = 1 - x_1 \qquad (6)$$

It will be appreciated that if only variations in moisture content are to be monitored then the temperature sensor 20 of the present embodiment may be omitted.

As is well known in the art, the relative humidity, Rh, is dependent on the total pressure $P_{TOT}$ of the monitored reference gas as well as the volume fraction, $x_2$, of the moisture. By optionally providing a pressure meter 22 (shown as broken lines in FIG. 1) in operable connection to the analyzer 18 then the analyzer 18 may be programmed to calculate the relative humidity Rh according to the equation:

$$Rh = \frac{p_{tot} \times x_2}{p_v^*} \qquad (7)$$

where $p_v^n$ is saturation vapor pressure which, for water, is a well-known function of the temperature T in degrees Celsius and may be expressed as:

$$p_v^* = e^{\left(12.03 - \frac{4025}{T+235}\right)} [bar] \qquad (8)$$

which value may also be calculated within a suitably programmed analyzer 18.

By including suitable known graphics processing circuitry within the analyzer 18 then a display unit 24 may be operably coupled to the analyzer 18 and driven by the circuitry to display the results of the analysis performed within the analyzer 18. The display unit 24 might for example show a numerical, graphical or other visual representation of the moisture volume fraction, $x_2$ or the relative humidity Rh or provide an indication that a change in moisture content has been detected.

Figure 2:
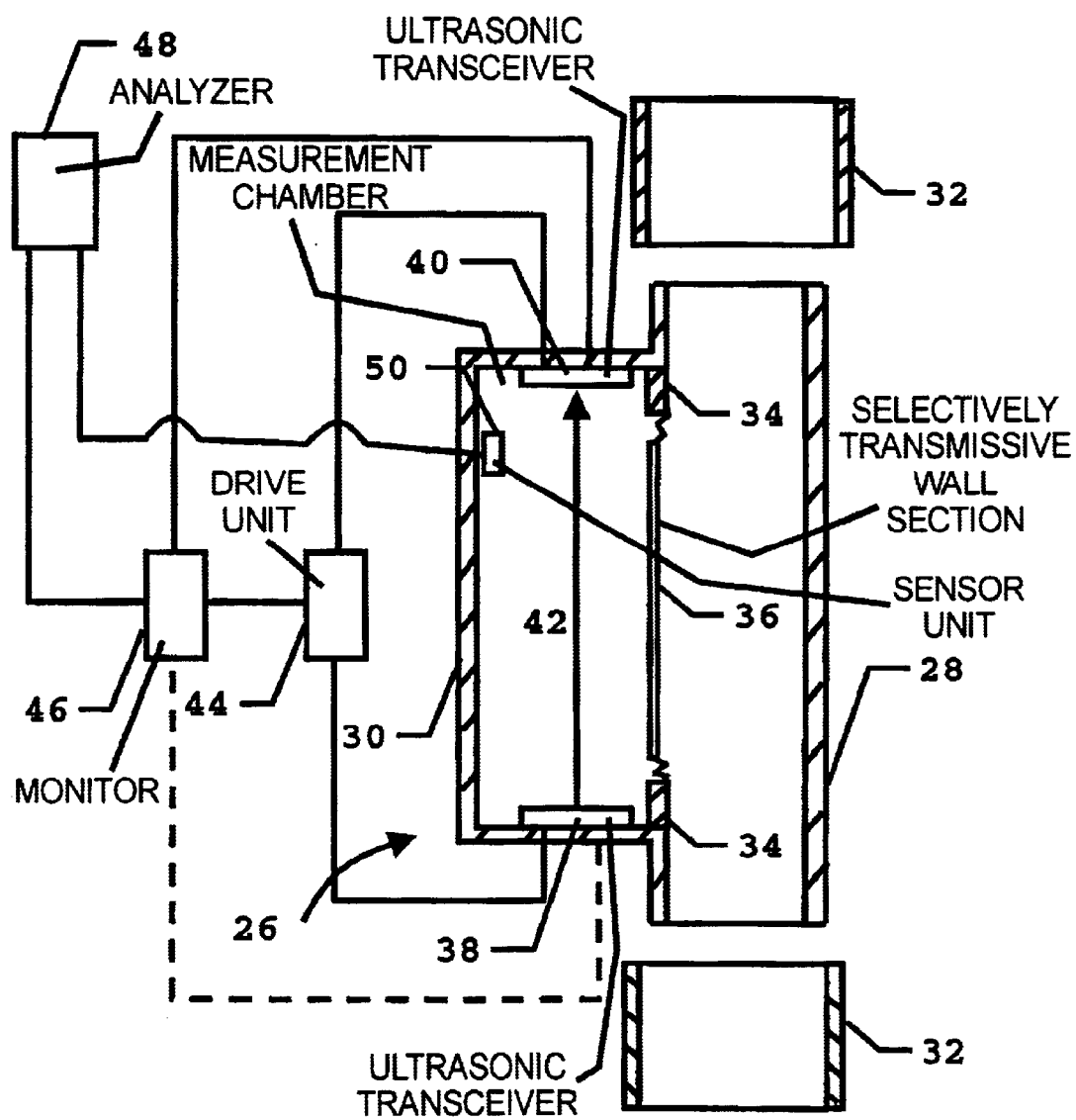
FIG. 2 shows an inventive acoustic gas monitor adapted for in-line connection with a flow conduit in which a host gas and a gaseous substance to be measured are intended to flow.

A further embodiment of an acoustic gas monitor according to the present invention is illustrated in FIG. 2. A housing 26 comprises a gas conduit portion 28 that provides a flow path through the housing 26 for a host gas containing a gaseous substance to be monitored and a gas measurement chamber 30. The gas conduit 28 is, in the present example, shown adapted for an in-line push-fit connection with an external gas conduit 32 that carries the host gas. The gas conduit 28 and the measurement chamber 30 are mutually configured with a common wall section 34, at least part 36 of which is formed of a material that is selectively permeable to the gaseous substance to be monitored (for example NAFION™ if moisture is to be monitored). The material of the part 36 of the common wall section 34 is usefully, although not essentially, formed as a flexible section that can move in response to pressure differences between gas within the monitoring chamber 30 and the host gas within the gas conduit 28. Alternatively, a separate movable wall section may be provided to move in response to the pressure difference.

A pair of acoustic transceivers 38,40 are acoustically coupled to internal the monitoring chamber 30 and are adapted to cooperate to define an acoustic path 42 along which acoustic waves propagate as one transceiver (38 say) of the pair is made to operate as an acoustic emitter and the other (40 say) as an acoustic receiver under control of a drive unit 44, in a manner well known in the art. The drive unit 44 may also be configured in a known manner to make the transceivers operate so as to cause the propagation of acoustic waves along the acoustic path 40 in the opposite direction (in the present example from the transceiver 40 to the transceiver 38). A monitor 46 is operably connected to the drive unit 44 and to the transceiver 40 (or transceivers—shown as broken line connection in FIG. 2) presently acting as the acoustic receiver. The monitor 46 is arranged to operate in a manner equivalent to the monitor 16 of FIG. 1 to provide a signal to an analyzer 48 indicative of the acoustic velocity V in the medium within the monitoring chamber 30.

The analyzer 48 is operably connected to a sensor unit 50 that provides as an input to the analyzer 48 a signal representing pressure $P_{TOT}$ and temperature T of the medium within the monitoring chamber 30. The analyzer 46 is configured to operate in a manner equivalent to that of the analyzer 18 of FIG. 1 to derive information on the level of gaseous substance to be monitored within the monitoring chamber 30.

For ease of explanation the drive units 14,44; the monitors 16,46; and the analyzers 18,48 are shown in FIG. 1 and FIG. 2 as physically separate units. However, it is to be understood that some are all of these units may be realized in a single, suitably programmed, microprocessor device equipped with known appropriate interface cards selected to permit one or both the control of and the communication with the remaining external devices in accordance with the invention.

Although modifications and changes may be suggested by those skilled in the art, it is the intention of the inventor to embody within the patent warranted hereon all changes and modifications as reasonably and properly come within the scope of his contribution to the art.

I claim as my invention:

1. An acoustic gas monitor comprising:

a measurement chamber for receiving a gaseous substance to be monitored;

an acoustic velocity meter acoustically coupled to an interior of said measurement chamber for determining an acoustic velocity, in said interior of said chamber, and generating an output signal indicative of said acoustic velocity; and said measurement chamber having a wall section for selective transmission of said gaseous substance between a reference gas in said interior of said measurement chamber and a host gas at an exterior of said chamber to allow said gaseous substance to be transported through said wall section between an interior and an exterior of the measurement chamber until respective concentrations of said gaseous substance at said interior and exterior equalize.

2. An acoustic gas monitor as claimed in claim 1 further comprising an analyzer connected to said acoustic velocity meter to receive said output, said analyzer determining from said output, information relating to a level of said gaseous substance in said measurement chamber.

3. An acoustic gas monitor as claimed in claim 1 wherein said wall section consists of a material which is selectively permeable to said gaseous substance.

4. An acoustic gas monitor as claimed in claim 3 wherein said wall section is movable in response to pressure difference between said interior and said exterior of said chamber in a direction to reduce said difference.

5. An acoustic gas monitor as claimed in claim 3 wherein said material is selectively permeable to water vapor.

6. An acoustic gas monitor as claimed in claim 1 further comprising a housing in which said measurement chamber is disposed, said housing having a gas flow conduit having a conduit wall in common with said measurement chamber, said conduit wall containing said wall section for the selected transmission of said gaseous substance.

7. An acoustic gas monitor as claimed in claim 6 wherein said wall section consists of material which is selectively permeable to said gaseous substance.

* * * * *